United States Patent [19]

Devlin et al.

[11] Patent Number: 5,562,693
[45] Date of Patent: Oct. 8, 1996

[54] CUTTING BLADE ASSEMBLY FOR A SURGICAL SCISSORS

[75] Inventors: Thomas E. Devlin, Brighton, Mass.; Kristin W. Grube, Indianapolis, Ind.

[73] Assignee: Alcon Laboratories, Inc., Fort Worth, Tex.

[21] Appl. No.: 514,160

[22] Filed: Aug. 11, 1995

[51] Int. Cl.⁶ .................................................. A61B 17/32
[52] U.S. Cl. ...................... 606/174; 606/166; 606/169; 606/170; 606/171; 128/751
[58] Field of Search ................................. 606/174, 166, 606/169, 171, 172, 13; 128/751, 754

[56] References Cited

U.S. PATENT DOCUMENTS

| | | |
|---|---|---|
| 4,201,213 | 5/1980 | Towsend .................................. 606/174 |
| 4,258,716 | 3/1981 | Sutherland . |
| 4,433,687 | 2/1984 | Burke et al. . |
| 4,877,026 | 10/1989 | de Laforcade . |
| 5,080,098 | 1/1992 | Willett et al. . |
| 5,263,958 | 11/1993 | deGuillebon et al. ................. 606/174 |
| 5,275,607 | 1/1994 | Lo et al. ................................. 606/174 |
| 5,350,391 | 9/1994 | Iacovelli .................................. 606/174 |
| 5,395,386 | 3/1995 | Slater ...................................... 606/174 |
| 5,443,476 | 8/1995 | Shapiro . |

*Primary Examiner*—Michael Powell Buiz
*Assistant Examiner*—Kevin Truong
*Attorney, Agent, or Firm*—Jeffrey S. Schira

[57] ABSTRACT

The present invention includes a stationary outer blade and a rotating inner cutting blade. A unique blade design and geometry allows clean, smooth cuts in fibrous tissue.

14 Claims, 3 Drawing Sheets

CUTTING BLADE ASSEMBLY FOR A SURGICAL SCISSORS

BACKGROUND OF THE INVENTION

The present invention relates to microsurgical instruments and more particularly to a blade design for an ophthalmic microsurgical scissors.

During ophthalmic microsurgery, it is often necessary to cut, delaminate and/or dissect thin, fibrous neovascular membranes located adjacent to the retina. The preferred device for cutting such membranes are microsurgical scissors. These scissors must be able to cut tissue cleanly, without grabbing or pulling the tissue because of the close proximity of the tissue to the retina. The blades of such microscissors must also be able to withstand extremely high loads without breaking.

U.S. Pat. Nos. 4,258,716 (Sutherland), 4,877,026 (deLaforcade) and 5,263,958 (deGuillebon, et al.) disclose microscissors suitable for ophthalmic surgery. None of these references, however, disclose the unique blade design of the present invention.

Accordingly, a need continues to exist for a microscissors that cuts cleanly and without grabbing the tissue being cut.

BRIEF DESCRIPTION OF THE INVENTION

The present invention includes a stationary outer blade and a rotating inner cutting blade. A unique blade design and geometry allows clean, smooth cuts in fibrous tissue.

Accordingly, one objective of the present invention is to provide a surgical scissors having a stationary outer blade and a rotating inner cutting blade.

Another objective of the present invention is to provide a surgical scissors that cuts fibrous tissue cleanly.

These and other objectives and advantages of the present invention will become apparent from the detailed description and claims which follow.

DETAILED DESCRIPTION OF THE INVENTION

Figure 1:
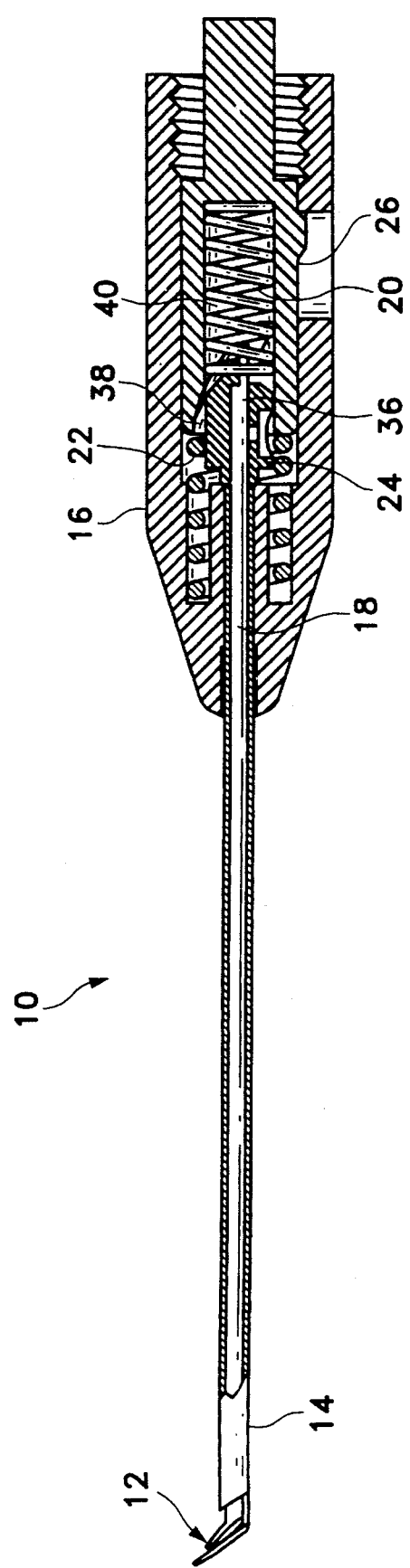
FIG. 1 is a cross sectional view of a surgical microscissors using the blade design of the present invention.

As can best be seen in FIG. 1, horizontal microscissors 10 generally include a blade assembly 12, an outer probe robe 14, housing 16, inner cutter robe 18 and a means for providing rotation of inner cutter rod 18 relative to outer probe robe 14. In the preferred embodiment illustrated in FIG. 1, rotation of inner cutter rod 18 is provided by spring 20, return spring 22, hub 24 and plunger 26 in a manner that will be described below. Other methods of rotating inner cutter rod 18, such as the assembly disclosed in U.S. Pat. No. 5,263,958 (deGuillebon, et al.) or the bell and crank assembly disclosed in U.S. Pat. No. 4,258,716 (Sutherland) may also be used.

Figure 3:
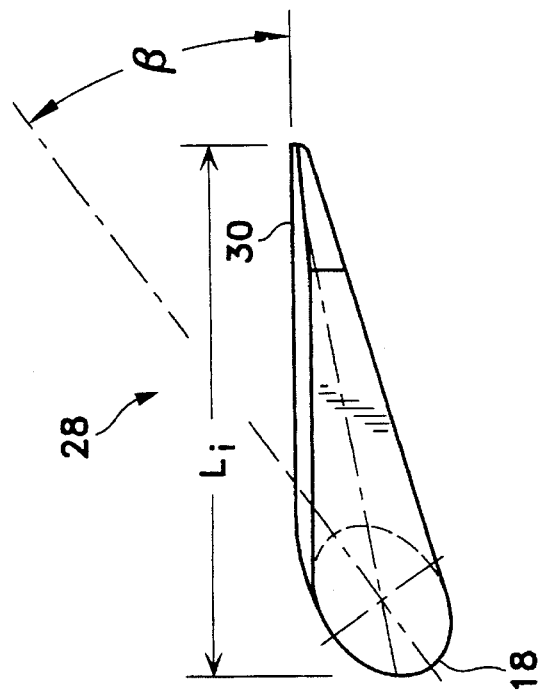
FIG. 3 is an enlarged plan view of the inner curing blade of the present invention.
Figure 2:
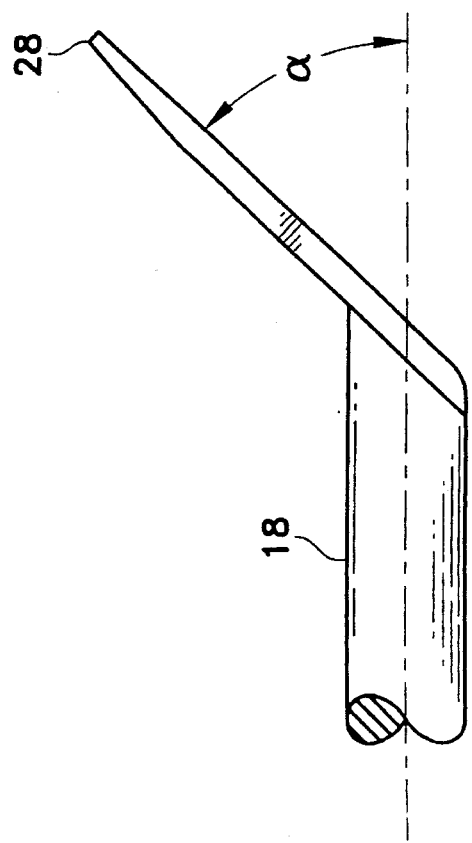
FIG. 2 is an enlarged elevational view of the inner blade assembly of the present invention.

As can be seen in FIGS. 2 and 3, inner cutting blade 28 is attached to inner cutter robe 18 at the distal end of rod 18. Blade 28 may be attached to rod 18 by any suitable method but welding or laser welding is preferred. Rod 18 is preferably made from 304 stainless steel with a nominal outside diameter of 0.0255 inches. Blade 28 preferably is made from 420 stainless steel with a hardness of between 48–52 Rc. Blade 28 preferably is between 0.007 inches and 0.009 inches thick with a length $L_i$ of between 0.05 inches and 0.15 inches. As can be seen in FIG. 2, blade 28 is attached to rod 18 at an angle $\alpha$ relative to the longitudinal axis of rod 18 of between 40° and 50°, with 45° 30' being preferred. As can be seen in FIG. 3, cutting edge 30 of blade 28 lays at an angle $\beta$ relative to the major axis of rod 18 (rod 18 being elliptical in cross section when cut at an angle). Angle $\beta$ preferably is between 30° and 40° with 35° 23' being more preferred.

Figure 5:
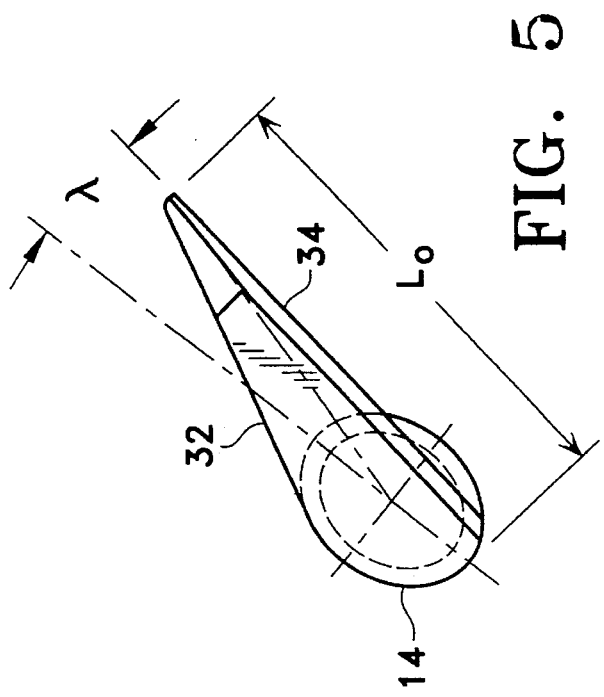
FIG. 5 is an enlarged plan view of the outer curing blade of the present invention.
Figure 4:
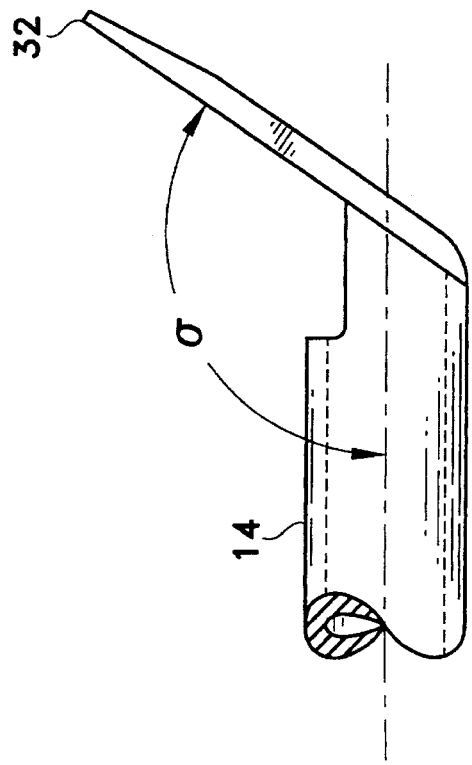
FIG. 4 is an enlarged elevational view of the outer blade assembly of the present invention.

As can be seen in FIGS. 4 and 5, outer cutting blade 32 is attached to outer probe tube 14 at the distal end of tube 14. Blade 32 may be attached to tube 14 by any suitable method but welding or laser welding is preferred. Tube 14 is preferably made from 304 stainless steel tubing with an outside diameter of between 0.0355 inches and 0.0360 inches and an inside diameter of between 0.0250 inches and 0.0265 inches. Blade 32 preferably is made from 420 stainless steel with a hardness of between 48–52 Rc. Blade 32 preferably is between 0.007 inches and 0.009 inches thick with a length $L_o$ of between 0.08 inches and 0.14 inches. As can be seen in FIG. 4, blade 32 is attached to tube 14 at an angle $\sigma$ relative to the longitudinal axis of tube 14 of between 120° and 130°, with 126° being preferred. As can be seen in FIG. 5, cutting edge 34 of blade 32 lays at an angle $\gamma$ relative to the major axis of tube 14 (tube 14 being elliptical in cross section when cut at an angle). Angle $\gamma$ preferably is between 5° and 10° with 7° 45' being more preferred.

Figure 6:
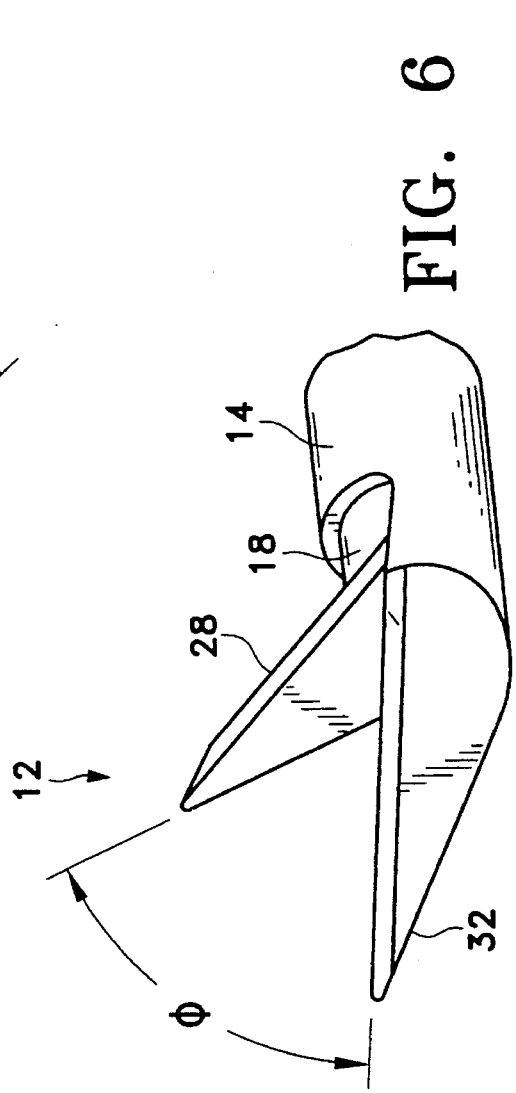
FIG. 6 is an enlarged end view of the curing blade assembly of the present invention.

As can be seen in FIGS. 1 and 6, the difference in angles $\alpha$ and $\sigma$ results in an inference fit between blades 28 and 32 that allows scissors 10 to make clean, smooth cuts in fibrous tissue. As seen in FIG. 6, for ophthalmic applications, it is preferred that when blades 28 and 32 are in the open position, angle $\Phi$ is at least 65°, although larger or smaller angles may also be used.

In use, rotation of rod 18 is accomplished through plunger 26 acting on hub 24. As can be seen in FIG. 1, proximal end 36 of rod 18 is fixed within hub 24 by any suitable method (for example, gluing). Hub 24 contains ears or tabs (not shown) that ride within spiral slots 38 cut into the interior surface of throat 40 in plunger 26. When plunger 26 is depressed, the tabs on hub 24 follows spiral slots 38, causing hub 24 and rod 18 to rotate.

This description is given for purposes of illustration and explanation. It will be apparent to those skilled in the relevant art that changes and modifications may be made to the invention described above without departing from its scope or spirit.

We claim:

1. A cutting blade assembly, comprising:
   a) an inner cutter rod;
   b) an outer probe tube;
   c) an inner cutting blade attached to the inner cutter rod at a first angle of between 40° and 50°; and
   d) and outer cutting blade attached to the outer probe tube at a second angle of between 120° and 130°.

2. The assembly of claim 1 wherein the first angle is 45° 30'.

3. The assembly of claim 1 wherein the second angle is 126°.

4. The assembly of claim 1 wherein the inner cutting blade has a first length of between 0.05 inches and 0.15 inches.

5. The assembly of claim 1 wherein the outer cutting blade has a length of between 0.08 inches and 0.14 inches.

6. The assembly of claim 1 wherein the inner cutter rod, the outer probe tube, the inner cutting blade and the outer cutting blade comprise stainless steel.

7. The assembly of claim 1 further comprising a means fixed to the inner cutting rod for rotating the inner cutter rod.

8. A cutting blade assembly, comprising:
   a) a stainless steel inner cutter rod;
   b) an outer probe tube;
   c) an inner cutting blade attached to the inner cutter rod at a first angle of between 40° and 50°;
   d) and outer cutting blade attached to the outer probe tube at a second angle of between 120° and 130°; and
   f) a means fixed to the inner cutting rod for rotating the inner cutter rod.

9. The assembly of claim 8 wherein the first angle is 45° 30'.

10. The assembly of claim 8 wherein the second angle is 126°.

11. The assembly of claim 8 wherein the inner cutting blade has a first length of between 0.05 inches and 0.15 inches.

12. The assembly of claim 8 wherein the outer cutting blade has a length of between 0.08 inches and 0.14 inches.

13. The assembly of claim 8 wherein the inner cutter rod, the outer probe tube, the inner cutting blade and the outer cutting blade comprise stainless steel.

14. The assembly of claim 8 wherein the inner cutting blade and the outer cutting blade have a thickness of between 0.007 inches and 0.009 inches.

* * * * *